United States Patent
Hallisey

(10) Patent No.: US 9,658,223 B2
(45) Date of Patent: May 23, 2017

(54) TEMPERATURE-INDEPENDENT, PORTABLE, AND RAPID FIELD DETECTION OF ANTIGENS

(71) Applicant: Olivia A Hallisey, Greenwich, CT (US)

(72) Inventor: Olivia A Hallisey, Greenwich, CT (US)

(*) Notice: Subject to any disclaimer, the term of this patent is extended or adjusted under 35 U.S.C. 154(b) by 0 days.

(21) Appl. No.: 14/826,118

(22) Filed: Aug. 13, 2015

(65) Prior Publication Data

US 2017/0045509 A1 Feb. 16, 2017

(51) Int. Cl.
*B01L 3/00* (2006.01)
*G01N 33/543* (2006.01)

(52) U.S. Cl.
CPC .............. *G01N 33/54386* (2013.01)

(58) Field of Classification Search
CPC .............. B01L 2300/0816; B01L 2300/0887
USPC ................................. 422/503, 502
See application file for complete search history.

(56) References Cited

U.S. PATENT DOCUMENTS

| | | | | |
|---|---|---|---|---|
| 4,756,884 A | * | 7/1988 | Hillman | B01F 5/0646 366/DIG. 3 |
| 2010/0029553 A1 | * | 2/2010 | Scheibel | C07K 14/43518 514/19.1 |

OTHER PUBLICATIONS

Baize, S et al. "Inflammatory Responses in Ebola Virus Infected Patients." Clinical and Experimental Immunology 128.1 (2002): 163-168. PMC . Web. Jun. 22, 2016.

Bhandari, Paridhi, Tanya Narahari, and Dhananjaya Dendukuri. "'FabChips': a versatile, fabric-based platform for low-cost, rapid and multiplexed diagnostics." Lab on a Chip 15 (2011): 2493-99. Print.

Fu, Elain, et al. "Controlled reagent transport in disposable 2D paper networks." Lab on a Chip 7 (2010): 918-20. Print.

Kaplan, David L., and Charu Vepari. "Silk as a biomaterial." Progress in Polymer Science 32.8-9 (2007): 991-1007. Print.

Kaufman, P. et al., "Visualization and Measurement of Flow in Two-dimensional Paper Networks". Lab on a Chip. 2010, 10, No. 19. 2614-2617.

Lu, Qiang, et al. "Stabilization and Release of Enzymes from Silk Films." Macromolecular Bioscience 10.4 (2010): 335-454. Print.

Lutz, B. R., Liang, T., Fu E., Ramachandran, S., Kauffman, P. Yager, P.et al., Dissolvable Fluidic Time Delays for Programming Multi-step Assays in Instrument-free Paper Diagnostics. Lab on a Chip. 2013, 13, No. 14. 2840-2847.

Lutz, Barry R., et al. "Two-dimensional paper networks: programmable fluidic disconnects for multi-step processes in shaped paper." Lab on a Chip 24 (2011): 4274-78. Print.

(Continued)

*Primary Examiner* — Natalia Levkovich
(74) *Attorney, Agent, or Firm* — Sunstein Kann Murphy & Timbers LLP

(57) ABSTRACT

A device for determining the presence of an antigen in a sample uses a substrate shaped to define a plurality of lateral flow channels and a detection region. Each lateral flow channel is associated with a load spot. The substrate includes, for each of the lateral flow channels, a fluid conducting medium, and, for the detection region, a fluid retaining medium. A first load spot receives a sample from the subject. Each of the other load spots uses a dried mixture of silk fibroin with a reagent. The detection region includes an antibody. A second load spot includes a secondary detection antibody. A third load spot includes a color reagent. The device implements an ELISA reaction when activated by sequentially placed aliquots of an aqueous solution.

8 Claims, 3 Drawing Sheets

(56) References Cited

OTHER PUBLICATIONS

Murphy, Amanda R., and David L. Kaplan. "Biomedical Applications of Chemically-Modified Silk Fibroin." Journal of materials chemistry 19.36 (2009): 6443-6450. PMC . Web. Jun. 22, 2016.
Omenetto, Fiorenzo G., and David L. Kaplan. "New Opportunities for an Ancient Material." Science 329.5991 (2010): 528-31. Print.
Rockwood, Danielle N., et al. "Materials fabrication from Bombyx mori silk fibroin." Nature Protocols 6.10 (2011): 1612-31. Print.
Wolchover, Natalie. "The Silk Renaissance." Seedmagazine.com . Seed Media Group, Sep. 17, 2010. Web. Jun. 22, 2016. <http://seedmagazine.com/content/article/the_silk_renaissance/>.
Alpha Diagnostic International Ebola ELISA kit (AE-320520-1) Antibody and visible detection reagents.
Alpha Diagnostic International Ebola Virus Nucleoprotein (EVNP15-R).
BIOTREND Cheikalien GmbH. General Elisa Kit [Material Safety Data Sheet].
"Tufts Silk Portfolio." Tufts Tech Transfer . Tufts University Office for Technology Transfer, 2014. Web. Jun. 22, 2016. <http://techtransfer.tufts.edu/tuftssilkportfolio/>.

* cited by examiner

TEMPERATURE-INDEPENDENT, PORTABLE, AND RAPID FIELD DETECTION OF ANTIGENS

TECHNICAL FIELD

The present invention relates to antigen detection systems, and more particularly to such systems using lateral flow methodologies

BACKGROUND ART

ELISA tests for the presence of an antigen are known in the prior art. See, for example:
(1) BIOTREND Cheikalien GmbH. General Elisa Kit [Material Safety Data Sheet]. Kaufman, P. et al., Visualization and Measurement of Flow in Two-dimensional Paper Networks. Lab Chip. 2010, 10, No. 19. 2614-2617
(2) Alpha Diagnostic International Ebola ELISA kit (AE-320500-1) Antibody and visible detection reagents, Alpha Diagnostic International Ebola Virus Nucleoprotein (EVNP15-R),
(3) https://www.abdserotec.com/an-introduction-to-elisa.html.

Additionally, lateral flow assay devices are known in the prior art. See, for example: (1) BIOTREND Cheikalien GmbH. General Elisa Kit [Material Safety Data Sheet]. Kaufman, P. et al., Visualization and Measurement of Flow in Two-dimensional Paper Networks. Lab Chip. 2010, 10, No. 19. 2614-2617
(2) Fu, E., et al., Controlled reagent transport in disposable 2D paper networks. Lab Chip. 2010, 10, No. 7. 918-920
(3) Lu, Q., Wang, X., Hu, X., Cebe, P., Omenetto, F. and Kaplan, D. L. (2010), Stabilization and Release of Enzymes from Silk Films. Macromol. Biosci., 10: 359-368. doi: 10.1002/mabi.200900388
(4) Lutz, B. R., Liang, T., Fu E., Ramachandran, S., Kauffman, P. Yager, P. et al., Dissolvable Fluidic Time Delays for Programming Multi-step Assays in Instrument-free Paper Diagnostics. Lab Chip. 2013, 13, No. 14. 2840-2847
(5) Lutz, B. R., et al., Two-dimensional paper networks: programmable fluidic disconnects for multi-step processes in shaped paper. Lab Chip. 2011, 11, No. 24. 4274-4278

Each of the references in this Background Art section is hereby incorporated herein by reference in its entirety. In case of any conflict or ambiguity created by such incorporation by reference, the text of the present Application, devoid of such incorporation, shall govern.

SUMMARY OF THE EMBODIMENTS

In accordance with one embodiment of the invention, there is provided a device for conducting an assay for the presence of a disease state in a subject, wherein the disease is characterized by the presence of an antigen in a sample from the subject. In this embodiment, the device substrate is shaped to define a plurality of lateral flow channels and a detection region. Each flow channel has an exterior end and an interior end, wherein the interior ends of the flow channels are fluidly coupled to the detection region, and each of the exterior ends is configured to receive an aqueous fluid in a load spot. The substrate includes, for each of the lateral flow channels, a fluid conducting medium, and, for the detection region, a fluid retaining medium. A first load spot of a first one of the lateral flow channels is configured to receive a sample from the subject, wherein the sample is to be assayed for presence of the antigen. The detection region is impregnated with a mixture of a first silk fibroin and a detection reagent including an antibody. A second load spot of a second one of the lateral flow channels is impregnated with a mixture of a second silk fibroin and a secondary detection antibody that is released when the second load spot receives an aliquot of an aqueous compound. A third load spot of a third one of the lateral flow channels is impregnated with a mixture of a third silk fibroin and a color reagent that is released when the third load spot receives the aliquot of an aqueous compound and that causes a change in color in the detection region in the presence of a combination of the antigen, if contained in the sample, the primary and secondary detection antibodies, and the color reagent. When the first load spot receives a sample from the subject that contains the antigen, and the second and third load spots are sequentially provided with aliquots of the aqueous compound, the components at each of the load spots sequentially react at the detection region after traversing the corresponding lateral flow channels to produce the change in color as an indicator of the presence of the antigen in the sample of the subject.

In a further related embodiment, a fourth load spot of a fourth one of the lateral flow channels is impregnated with a mixture of a fourth silk fibroin and a stop reagent, so that when the fourth load spot is provided sequentially with a selected aliquot of the aqueous compound after the second and third load spots have been provided with aliquots of the aqueous compound, the stop reagent traverses its corresponding flow channel to the detection region to stop the reaction and to effect a further color change at the detection region.

In another related embodiment, each fluid conducting medium is embodied using a porous stratum overlying a hydrophobic layer and the fluid retaining medium is embodied using the same porous stratum overlying the same hydrophobic layer. Optionally, the porous stratum is formed by filter paper.

Alternatively or in addition, the first silk fibroin, the second silk fibroin, and the third silk fibroin are substantially identical types of material. Also alternatively or in addition, the device includes a base layer underlying the hydrophobic layer to provide physical support to the device. Optionally, the base layer is a sheet of cardboard.

In another related embodiment, each load spot has a distinct geometric shape, to facilitate identification of each load spot.

Optionally, the flow channels are configured to produce a desired time of arrival of reagent at the detection area based on a specific schedule of application of the aliquots of aqueous compound.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Definitions. As used in this description and the accompanying claims, the following terms shall have the meanings indicated, unless the context otherwise requires:

A "fluid conducting medium" is a structure that is configured to conduct fluid from a load spot to a detection region. In one embodiment the fluid conducting medium is embodied using a porous stratum overlying a hydrophobic layer, which may serve as a substrate. The porous stratum is optionally embodied in filter paper. The hydrophobic layer of the substrate is optionally embodied using paper coated for receiving printed photographic images. Alternatively, the hydrophobic layer is embodied in a suitable plastic such as polyvinyl chloride, polyethylene, or polypropylene.

A "fluid retaining medium" is a structure configured to retain fluid received from a load spot via a fluid conducting medium. The fluid retaining medium can be implemented in a manner similar to the fluid conducting medium. Specifically in one embodiment the fluid retaining medium is embodied using a porous stratum overlying a hydrophobic layer, which may serve as a substrate. The porous stratum is optionally embodied in filter paper. The hydrophobic layer is optionally embodied using paper coated for receiving printed photographic images. Alternatively, the hydrophobic layer is embodied in a suitable plastic such as polyvinyl chloride, polyethylene, or polypropylene. Optionally the fluid retaining medium is identical in structure to the fluid conducting medium.

When a substrate "includes" a fluid conducting medium, the substrate itself may serve to conduct fluid or alternatively the substrate may be provided with a separate layer to conduct fluid.

A "load spot" is a portion of a lateral flow channel configured to receive a fluid. In various embodiments, some of the load spots are used additionally to store a reagent, the release of which is activated by the application of an aqueous fluid, and one of the load spots is used to receive an aqueous sample.

Figure 1:
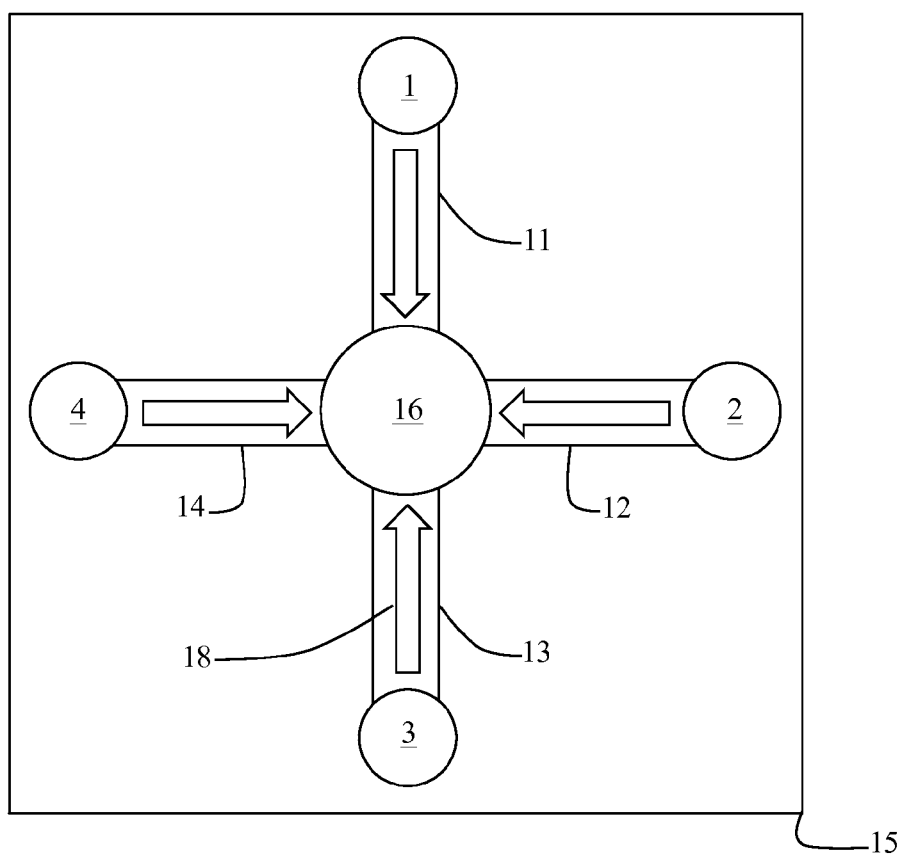
FIG. 1 is a schematic diagram of a device, in accordance with an embodiment of the present invention, for conducting an assay for the presence of an antigen in a sample from a subject.
Figure 2:
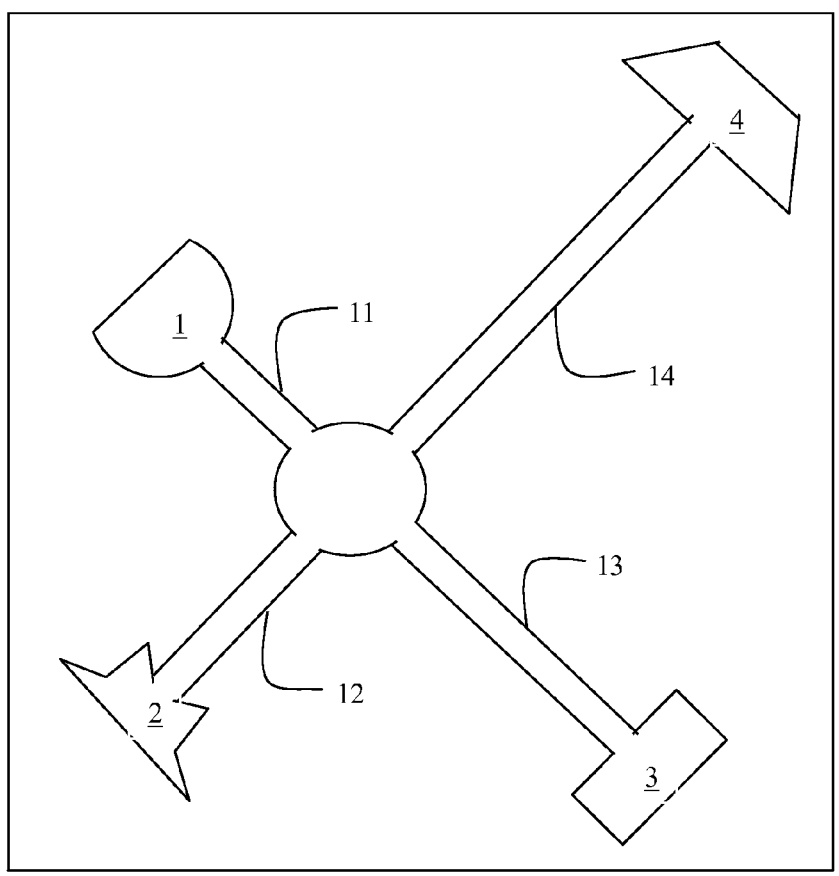
FIG. 2 is a schematic diagram of a device, in accordance with an embodiment of the present invention, similar to that of FIG. 1, but wherein the load spots are identified by geometric shape.
Figure 3:
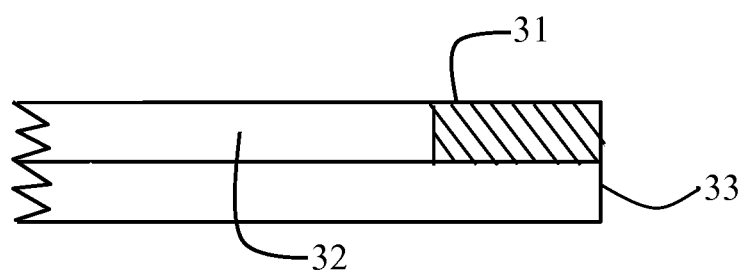
FIG. 3 is a vertical section of a lateral flow channel in accordance with an embodiment of the present invention, suitable for use in the embodiment of FIG. 2.

FIG. 1 is a schematic diagram of a device, in accordance with an embodiment of the present invention, for conducting an assay for the presence of an antigen in a sample from a subject. The device of this embodiment includes a series of load spots, identified as items 1, 2, 3, and 4. Each load spot is formed at an end of a corresponding flow channel, namely items 11, 12, 13, and 14 respectively. An aqueous fluid that is placed on any one of the load spots 1, 2, 3, or 4 travels along its corresponding flow channel to the detection area 16. The direction of this flow is indicated by arrow 18. The entire structure, including load spots 1, 2, 3, and 4, flow channels 11, 12, 13, and 14, and detection area 16 in this embodiment overlie a base layer 15, which is provided for support.

In practice, the sample to be assayed is in aqueous form and is placed on load spot 1. Examples of suitable samples include serum, saliva, nasal secretions, blood, semen, urine, etc. In various embodiments, load spots 2, 3, and 4 are impregnated with reagents. The impregnation is achieved by mixing a silk fibroin with an aqueous reagent, then applying the mixture to the load spot and allowing the load spot to dry. Causing the reagent to be present and mixed with silk fibroin has the effect of stabilizing the reagent for storage over an extended period of time and over a wide range of temperatures, while still preserving activity of the reagent. I have found that a wide range of reagents can be stabilized in this manner for activation when needed.

The fibroin was developed according to the following methodology.

*Bombyx mori* cocoons undamaged—(the fibroin will be extracted from these), ultrapure water, 0.02M Sodium Carbonate, Lithium Bromide (Sigma Aldrich), vacuum desiccator, 3-12 ml dialysis cassettes, Alpha Diagnostic International Ebola ELISA kit (AE-320500-1) Antibody and visible detection reagents, Alpha Diagnostic International Ebola Virus Nucleoprotein (EVNP15-R), Hewlett Packard Photographic Laserjet paper, Type 102 filter paper, PerkinElmer Spectrum One FTIR with an Attenuated Total Reflectance (ATR) accessory.

Methodology

I. Materials.

Fabrication from *Bombyx mori* Silk Fibroin: Silk fibroin is separated from commercially available silk cocoons as per Rockwood et. al.[11], with minor modifications, which are explained below. The following is a brief description of the methodology.

Cocoon Extraction (Day 1)

The cocoons will be cut with titanium scissors into dime-sized pieces and the dead silkworms will be thrown out.

Fibroin Extraction (Day 2)

A 1-liter glass beaker will be filled with 1 liter of ultrapure water which will be heated to a boil. 2.5 g of the cut cocoon pieces will be added and left in the water for 20 minutes. The silk fibroin is then removed, rinsed and squeezed, and placed in a 1-liter beaker filled with 1 liter of ultrapure water, and stirred for 20 minutes. This process is repeated 2 more times, so the fibroin will be rinsed a total of 3 times. The fibroin will be then spread on sheet of aluminum foil and left to dry under a fume hood overnight.

The same procedure is carried out, repeating the entire process (for day 2), with cooking times of 30, 45, and 60 minutes, to create silk fibroin solutions of varying molecular weights. The molecular weight of the fibroin is inversely related to the boiling time; i.e. a shorter boiling time of 20 minutes will produce a fibroin solution with greater molecular weight, and slower fluidic flow rates, when wet with ELISA reagents. It is this variation in cooking time, and subsequent control of the fluidic-wetting properties of the silk fibroin, that will act as a precursor for control of ELISA reagent chemistry sequences on the Ebola paper detection system. Cooking time, and antibody/detection reagent fluidic flow will be controlled via MW of the fibroin, to design a paper-ELISA based detection system. The timing of flow is controlled by factors including: (1) volume of chemicals used, (2) width or length of channels, and (3) timing/sequence of application of aqueous fluid.

Dissolving Silk Fibroin in LiBr. A 9.3M LiBr aqueous solution will be prepared. The silk fibroin will be packed into a 50 ml glass beaker and LiBr will be added, producing a solution that is 20% silk and 80% of 9.3M LiBr (by volume). The fibroin will be left to completely dissolve in an oven at 60° C. for 4 h.

Dialysis and Centrifugation. The dialysis cassettes will be hydrated in deionized water for approximately 5 minutes. With a 20-ml syringe and an 18-gauge needle, 12 ml of the silk-LiBr solution will be inserted into a 3-12-ml dialysis cassette and dialyzed (and stirred) against 1 liter of ultrapure water per 12 ml cassette. The water will be changed six times within 48 hours. The silk will be removed from the cassettes with another 20-ml syringe and an 18-gauge needle, and placed in a 50-ml conical tube. The silk in the tube will be centrifuged to remove impurities, at 9,000 r.p.m. (~12,700 g) at 4° C. for 20 min, poured with a 25 ml pipette into another centrifuge tube and centrifuged again the same way. This process will yield about 25 ml of 6-8% (wt/vol) of silk solution.

ATR-Fourier Transform Infrared Spectroscopy of Silk Solution. An Attenuated Total Reflectance Fourier Transform Infrared (ATR-FTIR) spectrum of the hosting (silk) medium is collected, so that stability of the Ebola ELISA reagents can be (later) established within that same medium, free of refrigeration. Briefly, 100 µl of the 30 minute (cook time) silk solution will be placed atop the diamond ATR crystal, and allowed to air dry, to remove water content.

ATR-FTIR is also used to verify that the chemical composition of the various cooking times remains constant, aside from changes in molecular weight. As expected, the FTIR spectra for the 20, 30, 45, and 60 minute silk-fibroin cook times are the same.

Creation and Evaluation of Liquid Fluidics for Silk Lateral-Flow Channels on Paper Substrates. 1. Selection of Paper Substrate for Lateral Flow Detection. The appropriate paper substrate must be selected, so that the silk film is created on top of the paper substrate, without chemically binding to the paper surface itself. In this way, fluidic motion of the water soluble Ebola ELISA reagents will occur within the silk film, lateral-flow strip, and not on the paper itself.

The 20, 30, 45, and 60 minute silk solutions are placed within 3 mm flow channels on various types of paper finishes, including photographic glossy, photographic mat, and Type 102 Filter Paper. The 3 mm flow channels are created using 50 µm thick, 3M painter's tape. The silk films are allowed to air dry for 1 hour, to create the hardened silk, shiny layer.

2. Scanning Electron Microscopy (SEM) of Dried Silk Thin Films on Paper. To determine which paper is best for creation of silk thin film, lateral-flow strips, SEM images were obtained for matted and shiny photographic papers, as well as the Type 102 filter paper. These SEM's were compared to those of the silk thin films created on each of those papers, to evaluate which paper substrate leads the creation of uniform silk thin films. SEM's were also used to evaluate dissolution of the dried silk thin films, once they have been water activated, so that embedded reagents are successfully released.

3. Measure of Lateral Flow as a Function of Paper Type, and silk cook time, using Water Soluble Marker Ink. For each paper type (i.e. shiny photographic, matte photographic, and Type 102 filter), water containing purple water soluble marker ink was used to evaluate water-soluble fluidics for each silk cook time (i.e. 20, 30, 45, and 60 minutes), to begin construct of a "card" lateral-flow detection system.

The device is used by sequentially invoking each of the load spots. For example, in constructing a device to assay the presence of Ebola antigen, load spot 1 is used for the sample. Load spot 2 includes a dried mixture of fibroin with Antihuman IgG HRP. Load spot 3 includes a dried mixture of fibroin with tetramethylbenzidine (TMB). Load spot 4 includes a dried mixture of 0.16 M sulfuric acid as the stop reagent. The detection area includes a dried mixture of fibroin with Ebola primary antibodies.

To use the device of FIG. 1, the sample is placed on load spot 1, and then aliquots of an aqueous solution are successively placed in load spots 2, 3, and 4, according to the timing set forth in Table 1 below.

TABLE 1

| STEP | TIME (in minutes) | PROCEDURE |
|------|-------------------|-----------|
| 1 | 0 | 30 ul of serum at load spot 1 |
| 2 | 15 | swab center detection zone with sterilized q-tip to remove free ebola antigens |
| 3 | 15 | put 30 ul of water on load spot 2 (releasing secondary detection antibody) |
| 4 | 22 | swab center detection zone with sterilized q-tip to remove free IgG HRP (secondary detection antibody) |
| 5 | 22 | put 30 ul of water on load spot 3 (releasing TMB substrate) |
| 6 | 25 | put 30 ul of water on load spot 4 (releasing stop solution) |
| 7 | 25 | positive result will be indicated by a yellow color change in center detection zone. Negative result will have no color change. |

This sequence of events causes the following series of events: (a) the sample travels down the flow channel 11 to the detection area, where any Ebola antigen in the sample reacts with the Ebola primary antibodies. (b) The Antihuman IgG HRP travels down flow channel 12 to the detection area to react with any bound antigen-antibody complex resulting from step (a). (c) The Tetramethylbenzidine (TMB) travels down flow channel 13 to the detection area to react with any complex resulting from step (b) and produces a color reaction in the presence of such a complex. (d) The stop reagent travels down flow channel 14 to the detection area to react with any complex produced in step (c), so as to stop further reaction and to provide an enhanced color change when antigen is present in the sample.

It will be apparent that the reagents chosen for use in various embodiments of the present invention are typically those suitable for use in a traditional sandwich ELISA assay. (For further information concerning the ELISA assay, see the references recited in the Background Art section of this application.) However, in the present context, the ELISA reagents, as previously discussed, are placed in a different environment that includes silk fibroin and is dried. Also as previously discussed, this environment allows the device to be stored for an extended period of time, over a wide range of temperatures, without adversely affecting operation of the device and the efficacy of the reagents used in it. Additionally, compared with conventional environments, various embodiments of the present invention allow simple user control of timing of the sequence of reactions of the reagents simply by timing of the application of aliquots of aqueous solution to each of the load spots.

Insertion of the Ebola ELISA reagents to the silk lateral-flow channels. Once the optimum paper type and aqueous fluidics as a function of silk cook time are established, the reagents from the Alpha Diagnostic International's Ebola Human Anti-ZEBOV ELISA kit (AE-320500-1) and ELISA EVNP15-R Ebola NP are added to the liquid silk prior to creation of the lateral flow strips.

Evaluation of the Stability of the Ebola ELISA reagents dissolved in deionized water (typical preparation) and in silk fibroin, when stored at Room Temperature. Ebola Human Anti-ZEBOV ELISA kit reagents are freshly prepared, as per instruction where all dilutions are made with deionized water. Additionally, the same dilutions are carried out in the (prepared) silk fibroin solution. Both water-dissolved and silk fibroin-dissolved ELISA reagents are then stored at room temperature for 1 week. On a daily basis, ELISA detection of 1, 2.5, 5, and 10 U/ml calibration standards, as well as a 0.5 U/ml positive control sample (500 pg/ml Ebola NP Antigen), are carried out in a 96-wellplate format using a Molecular Devices $V_{max}$ plate reader, with 450 nm (−650 nm background) detection. Expected trending of calibration standards, as well as the ability to detect levels of Ebola antigen typical of asymptomatic patients (500 pg/ml) are used to determine the efficacy of detection for both water and silk fibroin dissolved preparations.

Construction of the Field Ebola Detection System. Four silk derived lateral-flow channels containing the pre-embedded ELISA reagents are placed within a single "card" configuration, where all channels are directed towards a visual detection center. The wetting of the reagents with di-water and Ebola Nucleoprotein (EVNP15-R) at opposite ends of the lateral-flow channels will cause a timed arrival of the reagents at the center that mimics the sequence of the sandwich ELISA kit.

Initially, reagents are encased in silk fibroin at the tip of three of the channels and subsequently activated by the user with the application of water (an aqueous fluid), which dissolves the silk and initiates a sequential, timed-release flow towards a center detection zone, where a positive (colored) result confirms the presence of Ebola control antigens.

Each "tip" ("load spot") and its corresponding sample and/or reagent may be distinguished by a distinctly patterned shape for additional ease of use. Into each of the four load spots are placed items as follows:

Channel #1: Serum Sample

Channel #2: Anti-human secondary antibody IgG (Immunoglobulin G) HRP, Peroxide-Mouse Anti-Human IgG Invitrogen Monoclonal Mouse Antibody Reagent Liquid. An enzyme conjugate stabilizer, it contains 0.1% proclin as preservative.

Channel #3: TMB 3,3',5,5'-Tetramethylbenzidine (TMB). Chromogenic substrate used in immunohistochemistry staining procedures and a reagent used in enzyme-linked immunosorbent assays (ELISA). TMB is a substrate for horseradish peroxidase which produces a soluble blue reaction product that may be read at 370 or 655 nm. Acid will stop the reaction and will form a yellow reaction product for endpoint assays.

Channel #4: STOP solution (0.16M sulfuric acid)

Center detection zone: Ebola primary antibodies

Sandwich ELISA Detection of Ebola Antigens. Detection of the presence of Ebola is based on visual color change of the lateral-flow target. 30 ul of an aqueous fluid is added to each load spot, in order of shortest to longest flow channel (1, 2, 3, & 4), so that "color" arrives at the detection zone in the desired order for Ebola ELISA detection.

FIG. 2 is a schematic diagram of a device, in accordance with an embodiment of the present invention, similar to that of FIG. 1, but wherein the load spots are identified by geometric shape. In this case load spot 1 is shown as a semi-circle, load spot 2 is shown as an irregular polygon, load spot 3 is shown as a rectangle, and load spot 4 is shown as a trapezoid. As explained in connection with Table 1, it is of critical importance to place aliquots of aqueous solution in each load spot in a properly ordered and timed sequence. Identifying each of the load spots by geometric shape facilitates proper ordering and timing of application of the aliquots of aqueous solution. In implementing a prototype embodiment of the present invention, I have found it convenient to construct each flow channel by using a layer of filter paper (to provide a fluid path) over a layer of photo-paper (to provide a hydrophobic layer), these items were laser cut to assure alignment. The same configuration and, indeed, the same layers were used to implement the detection area and the load spots. However, as previously described the detection area and the load spots (other than load spot 1) were impregnated with a mixture of fibroin and reagent. The entire arrangement of detection area, flow channels, and load spots was mounted on a base layer 15 of cardboard for support.

Although in one embodiment, each of the flow channels, 11, 12, 13, and 14 is of the same length, in another embodiment, the geometry of the flow channels can be altered to support a different timing of application of the aliquots of aqueous solution. For example, if all of the aliquots are applied at substantially the same time (or at different scheduled intervals), the flow channels 11, 12, 13, and 14, can be configured so that fluid arrives at the detection area 16 sequentially from channels 11, 12, 13, and 14. Thus, the path length of channel 11 would be the shortest and the path length of channel 14 would be the longest, with the path length of channel 12 being longer than that of 11, but shorter than that of 13.

In yet another embodiment, the channels are coated with suitable agents to modulate the rate of flow, also with the same goal of adjusting the time of arrival of reagent from each of the load spots.

FIG. 3 is a vertical section of a lateral flow channel in accordance with an embodiment of the present invention, suitable for use in the embodiment of FIG. 2. Layer 32 of FIG. 3 corresponds to the filter paper discussed in connection with FIG. 2. Similarly layer 33 corresponds to the photo paper discussed in connection with FIG. 2. A load spot 31 is implemented, in the manner described above, by mixing silk fibroin with a reagent and applying the mixture to the filter paper at the location of the load spot, and allowing the treated filter paper to dry, producing a film that is a dried mixture of fibroin with reagent. (For load spot 1, as previously discussed, no reagent and no fibroin is required, since sample is applied at this location.)

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A device for conducting an assay for the presence of a disease state in a subject, the disease characterized by the presence of an antigen in a sample from the subject, the device comprising:

(a) a sub strate;

(b) at least three lateral flow paths, each flow path formed by a porous fluid conducting medium on the substrate, wherein each fluid conducting medium includes a porous stratum overlying a hydrophobic layer; each flow path having an exterior end and an interior end;

(c) a detection region, formed by a porous fluid retaining medium on the substrate;

wherein the interior ends of the flow paths are fluidly coupled to the detection region and the detection region therefore lies at a junction of the flow paths, the fluid retaining medium including the same porous stratum overlying the same hydrophobic layer; and (d) first, second, and third load spots formed on the substrate, each load spot being at a corresponding one of the exterior ends of the flow paths and configured to receive an aqueous fluid;

wherein the first load spot is configured to receive a sample from the subject, wherein the sample is to be assayed for presence of the antigen;

wherein the detection region includes a first mixture of a first silk fibroin and a detection reagent including an antibody, the first mixture forming a first silk film in the detection region;

wherein the second load spot includes a second mixture of a second silk fibroin and a secondary detection antibody that is released when the second load spot receives an aliquot of an aqueous compound, the second mixture forming a second silk film in the second load spot; and wherein the third load spot includes a third mixture of a third silk fibroin and a color reagent that is released when the third load spot receives the aliquot of an aqueous compound, and that causes a change in color in the detection region in the presence of a combination of the antigen, if contained in the sample, the primary and secondary detection antibodies, and the color reagent, the third mixture forming a third silk film in the third load spot;

so that when the first load spot receives a sample from the subject that contains the antigen, and the second and third load spots are sequentially provided with aliquots of the aqueous compound, the components at each of the load spots sequentially react at the detection region after traversing the corresponding lateral flow paths to produce the change in color as an indicator of the presence of the antigen in the sample of the subject.

2. A device according to claim 1, wherein the device has at least four lateral flow paths, and a fourth load spot of a fourth one of the lateral flow paths includes a fourth mixture of a fourth silk fibroin and a stop reagent, the fourth mixture forming a fourth silk film in the fourth load spot, so that when the fourth load spot is provided sequentially with a selected aliquot of the aqueous compound after the second and third load spots have been provided with aliquots of the aqueous compound, the stop reagent traverses its corresponding flow path to the detection region to stop the reaction and to effect a further color change at the detection region.

3. A device according to claim 1, wherein the porous stratum includes filter paper.

4. A device according to claim 1, wherein the first silk fibroin, the second silk fibroin, and the third silk fibroin are substantially identical types of material.

5. A device according to claim 1, wherein the substrate includes a base layer underlying the hydrophobic layer to provide physical support to the device.

6. A device according to claim 5, wherein the base layer is a sheet of cardboard.

7. A device according to claim 1, wherein each load spot has a distinct geometric shape, to facilitate identification of each load spot.

8. A device according to claim 1, wherein the flow paths are dimensioned to produce a desired time of arrival of reagent at the detection area based on a specific schedule of application of the aliquots of aqueous compound.

* * * * *

UNITED STATES PATENT AND TRADEMARK OFFICE
CERTIFICATE OF CORRECTION

PATENT NO. : 9,658,223 B2
APPLICATION NO. : 14/826118
DATED : May 23, 2017
INVENTOR(S) : Olivia A. Hallisey Page 1 of 1

It is certified that error appears in the above-identified patent and that said Letters Patent is hereby corrected as shown below:

In the Claims

In Column 8, Line 55 replace "(a) a sub strate;" with "(a) a substrate;"

Signed and Sealed this
Thirty-first Day of October, 2017

Joseph Matal
*Performing the Functions and Duties of the
Under Secretary of Commerce for Intellectual Property and
Director of the United States Patent and Trademark Office*